(12) United States Patent
Pfeiffer

(10) Patent No.: US 10,625,090 B2
(45) Date of Patent: Apr. 21, 2020

(54) MAGNETIC FIELD THERAPY APPARATUS, AND METHOD FOR GENERATING A MAGNETIC FIELD

(71) Applicant: Knut Pfeiffer, Munich (DE)

(72) Inventor: Knut Pfeiffer, Munich (DE)

( * ) Notice: Subject to any disclaimer, the term of this patent is extended or adjusted under 35 U.S.C. 154(b) by 229 days.

(21) Appl. No.: 15/526,273

(22) PCT Filed: Nov. 13, 2014

(86) PCT No.: PCT/EP2014/074497
§ 371 (c)(1),
(2) Date: May 11, 2017

(87) PCT Pub. No.: WO2016/074726
PCT Pub. Date: May 19, 2016

(65) Prior Publication Data
US 2017/0304643 A1    Oct. 26, 2017

(51) Int. Cl.
*A61N 2/02* (2006.01)
*A61N 2/00* (2006.01)

(52) U.S. Cl.
CPC ............... *A61N 2/02* (2013.01); *A61N 2/004* (2013.01)

(58) Field of Classification Search
CPC .................................. A61N 2/004; A61N 2/02
See application file for complete search history.

(56) References Cited

FOREIGN PATENT DOCUMENTS

DE    102009017229 A1    10/2010

OTHER PUBLICATIONS

DE102009017229A1, Google translation in English (Year: 2009).*
International Search Report and Written Opinion dated Jul. 29, 2015 for corresponding PCT Application No. PCT/EP2014/074497.

* cited by examiner

*Primary Examiner* — Christine H Matthews
(74) *Attorney, Agent, or Firm* — Kinney & Lange, P.A.

(57) ABSTRACT

A magnetic field therapy apparatus includes a magnetic field generation device for generating a magnetic field that can be applied to a patient, and a control device for controlling an intensity of the magnetic field in such a way that the magnetic field intensity increases incrementally during a first interval $T_1$ and is set to a constant level during a second interval ($T_2$), the ratio of the first interval $T_1$ to the second interval $T_2$ corresponding to the golden section +/−0.1, preferably +/−0.01.

20 Claims, 2 Drawing Sheets

MAGNETIC FIELD THERAPY APPARATUS, AND METHOD FOR GENERATING A MAGNETIC FIELD

BACKGROUND

The invention relates to a magnetic field therapy apparatus, comprising a magnetic field generating apparatus for generating a magnetic field which can be applied to a patient, and a control apparatus for controlling a field strength of the magnetic field such that a stepwise increase of the magnetic field strength takes place, as well as a method for generating a magnetic field in which a magnetic field strength is gradually increased.

A generic magnetic field therapy apparatus is known from DE 10 2009 017 229 A1.

The apparatus according to DE 10 2009 017 229 A1 comprises means which are designed in such a way that a magnetic signal can be generated and applied to a patient. The temporal progression of the generatable magnetic signal includes a gradual increase in the magnetic field strength. The magnetic field strength increases after certain time intervals by certain field strength increments. Overall, it has been found that the apparatus according to DE 10 2009 017 229 A1 can be used to increase the well-being of patients. However, the effectiveness of the magnetic field therapy apparatus is still considered to be improvable.

It is therefore one object of the invention to further increase the effectiveness of a magnetic field therapy apparatus and a corresponding method, in particular to increase the well-being of patients and/or to accelerate healing processes and/or to counteract diseases.

SUMMARY

A magnetic field therapy apparatus includes a magnetic field generating apparatus for generating a magnetic field which can be applied to a patient, and a control apparatus for controlling a field strength of the magnetic field such that a stepwise increase of the magnetic field strength takes place during a first period and during a second period (following the first period) a constant field strength is set, wherein the ratio of the first period to the second period corresponds to the golden section +/−0.1, preferably +/−0.01, still further preferably +/−0.005, still more preferably +/−0.001, and even more preferably (exactly) the golden section.

An important concept of the present disclosure is to provide a magnetic signal with a constant field strength after a signal with a stepwise increased magnetic field strength. A ratio of the period in which a stepwise increase in the magnetic field strength occurs and the period in which a constant field strength is set is set according to the golden section. With such an adjustment of the time periods, it has been shown in a surprising manner that the well-being of the patient can be increased particularly effectively. Furthermore, healing processes could be accelerated as well as diseases could be countered. In particular, it has been found that effective stress and stress-induced diseases can be effectively countered. Muscle tension could be alleviated. Attention deficits or learning difficulties could be reduced. Furthermore, the magnetic field therapy apparatus has also proved effective for the control of rheumatism and migraine.

The use of the magnetic field therapy apparatus for one or more of the above indications is disclosed herein as an independent inventive concept.

The golden section is usually regarded (as in the present context) as the division ratio of a variable (in the present case a period) in which the ratio of the whole to its larger part (in the present case the first period) corresponds to the ratio of the larger to the smaller (in the present case the second period). Expressed as a formula (with $T_1$ as the first period and $T_2$ as the second period), the following applies:

$$(T_1+T_2)/T_1 = T_1/T_2$$

The golden section is an irrational number, i.e. a number which can not be represented as a fraction of integers. The Greek letter $\phi$ is used as a mathematical symbol for this number (as in the present context). 99 as the irrational number can not be represented as a finite decimal fraction. A value of $\phi=1.6180339887$ is obtained rounded to the tenth decimal place.

The present disclosure is fundamentally based on the realization that numerous (anatomical) structures of the human body are designed in a golden section. From this it can be concluded that spatial proportions according to the golden section have an advantageous effect. The transfer of this knowledge to a temporal proportion, i.e. the adjustment of the ratio of the two periods according to the golden section, ultimately results from intuitive considerations. The efficacy was initially suspected, but could then also be checked due to the reaction of patients.

The incremental increase in the first period preferably includes at least three, more preferably at least five, increment steps. An upper limit of the increment steps can be 20 steps or 8 steps for example. Overall, a staircase signal can be formed, wherein each stair step corresponds to an increasing step. The period between two consecutive increment steps can be constant (or vary). The increase in field strength may also be constant (or vary).

In a specific embodiment, at least one battery (in particular at least one rechargeable battery) can be provided in order to provide a direct current for generating the magnetic field. As a result, the magnetic field strength can be set particularly precisely and, in particular, short current peaks which occur during a rectification of a mains alternating current can be avoided. Overall, the effectiveness of the magnetic field therapy apparatus is thereby increased.

In a further development, the control apparatus is designed for readjusting the magnetic field strength. Such a measure also improves the accuracy and constancy of the applied magnetic field, which increases the efficiency of the magnetic field therapy apparatus. A magnetometer can be provided in order to measure the applied magnetic field and to base the control thereon. For example, the magnetometer can be a Hall sensor.

In a concrete embodiment, a shielding device is provided for shielding electromagnetic fields. Preferably, the shielding device comprises at least one perforated plate. Alternatively or additionally, the shielding device can comprise a fabric web. In a specific further development, the shielding device can be designed (at least partially) as a tent. Furthermore, the shielding can be designed as an enclosure, wherein the treatment site for the patient is located within the enclosure. Overall, external electromagnetic fields can be effectively shielded from the patient or from the treatment site at which the generated magnetic signal is applied. External electromagnetic fields such as, for example, electrosmog, which could interfere with the treatment or application of the generated electromagnetic signal, can be blocked with the shielding. The effectiveness of the magnetic field therapy device is also further increased by such a measure.

The shielding device is particularly preferably constructed from perforated plates (or comprises such perforated plates). As a result, an electromagnetic shielding is achieved in a synergistic manner on the one hand, and on the other hand a sound reduction, since the perforated plates act as Helmholtz resonators. For this purpose, the individual holes may have a circular (or alternatively elliptical or rectangular) cross-section. Overall, a plurality of holes is provided, preferably at least 100, more preferably at least 1,000. A surface of the perforated plates defined by the holes can be 5% to 50%, preferably 7% to 20% of the total area of the perforated plates. The holes can have a diameter of 2 mm to 5 mm. The further development of the magnetic field therapy apparatus comprising at least one perforated plate or the formation of a shielding from at least one perforated plate a separate, independent idea (in particular also independent of the realisation of a golden section with respect to the first or second period). In particular, a combination of a magnetic signal which is incrementally increased (with the preceding and following further developments) together with a shielding comprising a perforated plate or composed (at least partially) of perforated plates is hereby disclosed as an independent inventive concept.

The time courses of the magnetic field strength in the first period may comprise an increase in the magnetic field strength by specific (in particular constant) field strength increments after certain (in particular constant) time intervals. In an alternative embodiment, it is possible for the magnetic field strength to be increased by different field strength increments after identical time intervals.

The generatable magnetic field strengths can be between 0 µT and 150 µT. Alternatively or additionally, the incremental increments for the magnetic field strength can be between 2 µT and 60 µT. Alternatively or additionally, the time intervals between the increasing steps can be between 5 and 8 seconds. It has been found that with such time courses of the magnetic field, an increase in the well-being of the patient can be achieved particularly effectively.

In general, the generatable magnetic field strength is preferably of the order of magnitude of the earth's magnetic field. The applicable magnetic field strength has a generally stepped or staircase-like course.

The field strength in the second period is preferably 15 to 40 µT, 20 to 30 µT, more preferably 25.12 µT. With such a field strength, the well-being of the patient is also effectively increased.

The first period may be 28 to 58 seconds, preferably 38 to 48 seconds, in particular 43 seconds. A cycle from the first and second time period can be repeated. Preferably, a repetition of the cycle (comprising the first and the second period) is performed 40 to 58 times, in particular 49 times, in a first embodiment. In a second embodiment, there are 30 to 42, preferably 37, repetitions.

A total duration of the application can last 50 to 66 minutes, in particular 58.09 minutes, in a first embodiment. In a second embodiment, the application time can last 30 to 42 minutes, in particular 36.75 minutes. The well-being of the patient is effectively increased by such values.

The field strength in the second period can be 5 to 13 times, in particular 8 to 10 times, as large as the field strength of a minimum step in the first period. Alternatively or additionally, the field strength in the second period may be 0.15 to 0.40, in particular 0.25 to 0.3 times as large as the field strength of a maximum stage in the first period.

In a specific embodiment, the magnetic field generating apparatus comprises at least one, preferably at least two or exactly two conductor coils. Further preferably, a first coil is formed elliptically or ovally. Alternatively or additionally, a first coil can have a (longer) diameter of 1.5 to 2.0 meters, in particular 1.70 to 1.80 meters. Alternatively or additionally, a second coil can be provided, which preferably has an (approximately) round cross-section. Alternatively or additionally, the second coil can have a cross-section which is smaller than the smaller cross-section of the first coil. A central region of one or more of the coils can be arranged in the abdominal region (solar plexus) of the patient. In a round configuration of the coil, the central region is defined by the center point. In an elliptical configuration of the coil, the central region is defined by a center point of a connecting line of the two ellipse focal points. A longer diameter of the first coil may correspond (approximately) to the size of a patient. The second coil is preferably (completely) arranged within a central third of a lying surface of the patient.

The above-mentioned object is further achieved by a method for generating a magnetic field (in particular using the magnetic field therapy apparatus of the type described above), in which a magnetic field strength is increased stepwise in a first period and a constant magnetic field strength is generated in a second period, wherein a ratio of the first to the second period corresponds to the golden section +/−0.1, preferably +/−0.01, still more preferably +/−0.005, still further preferably +/−0.001. The application of such a method to a patient can effectively increase their well-being. In particular, it has been found that stress and stress-induced disorders, muscle tension, attention deficits or learning disabilities, rheumatism and migraine can be treated effectively.

Preferably, the magnetic field strength in the first period is increased by specific field strength increments after certain (in particular constant) time intervals. Further preferably, the increase in the magnetic field strength in the first time period is carried out respectively after the same time intervals and/or is increased by the same field strength increments. In a specific embodiment, the magnetic field strength is increased by different field strength increments after the same time intervals.

Preferably, the field strength is readjusted. For this purpose, a measurement of the magnetic field strength, for example by a Hall sensor, can be carried out.

The field strength in the second period may be between 15 and 40 µT, preferably 20 to 30 µT, more preferably 25.12 µT. The first period can be set to 28 to 58 seconds, preferably 38 to 48 seconds, in particular 43.96 seconds. A cycle comprising the first and second period may be repeated. A cycle can preferably be repeated 40 to 58 times, in particular 49 times. In an alternative embodiment, the cycle can be repeated 30 to 42 times, preferably 31 times. The total application time may be from 50 to 66 minutes, in particular 58.09 minutes. In an alternative embodiment, the total duration of the application may be from 30 to 42 minutes, preferably 36.75 minutes. The field strength in the second period can be 5 to 13 times, in particular 8 to 10 times as large as the field strength of a minimum stage in the first period and/or as the field strength difference between two successive field strength steps. Furthermore, the field strength in the first period can be 0.15 to 0.40, in particular 0.25 to 0.30 times as large as the field strength of a maximum stage in the first period.

The current for generating the magnetic field is preferably fed from a battery.

BRIEF DESCRIPTION OF THE DRAWINGS

The invention is also described below with reference to further features and advantages with reference to an exemplary embodiment which is explained in more detail by reference to the drawings, wherein.

In the following description, the same reference numerals are used for identical and interacting parts.

DETAILED DESCRIPTION

Figure 1:
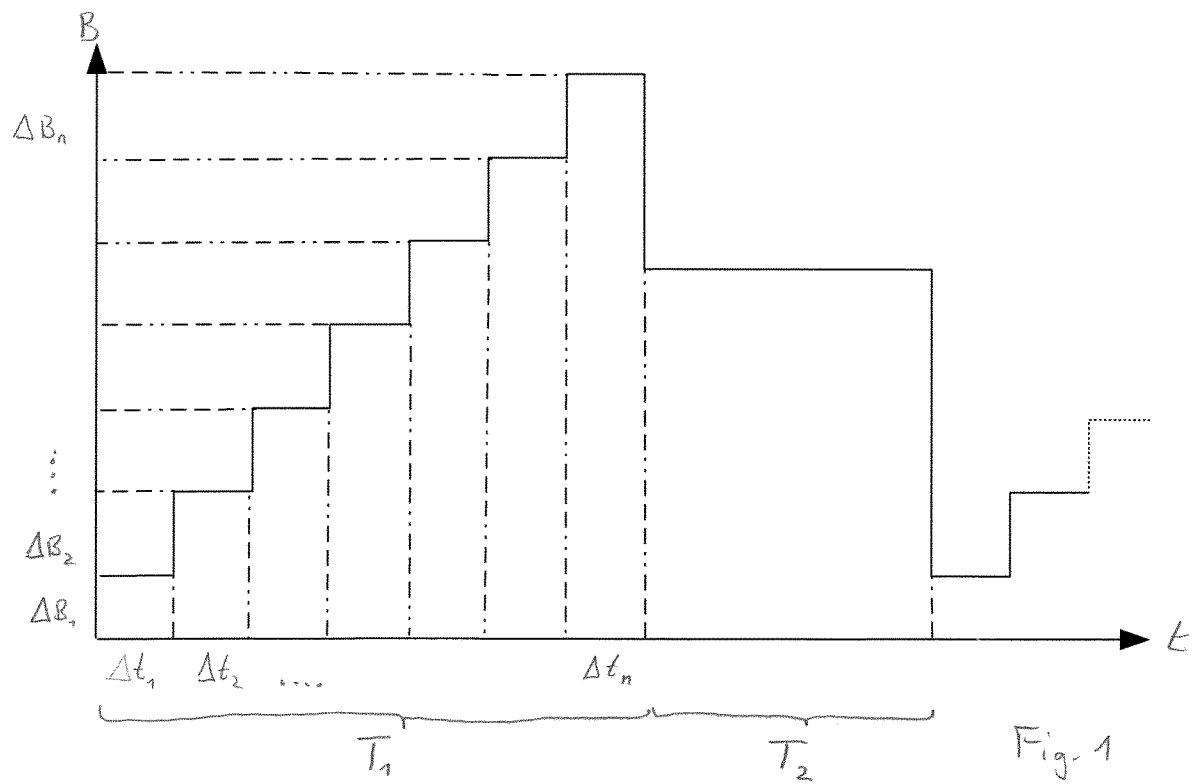
FIG. 1 shows a progression of the magnetic field strength B (t) in accordance with an embodiment of the invention.

FIG. 1 shows a magnetic signal B (t) generated by an apparatus according to an embodiment of the invention. The magnetic field strength B (t) increases in the course of time in steps or stairs. After time intervals $\Delta t_1$, $\Delta t_2$, ... $\Delta t_n$, the field strength increases by field strength increments $\Delta B_1$, $\Delta B_2$, ... $\Delta B_n$. A control apparatus (not shown) controls the generation of the magnetic field strength and its temporal course B (t). An essential component of the control unit is a programmable module with which a stair-shaped field strength signal B (t) can be generated within a first period $T_1$ as well as a constant field strength signal within a time period $T_2$. For example, the following signal course is generated:

6.28 seconds B=3.14 µT, then
6.28 seconds B=9.42 µT, then
6.28 seconds B=15.7 µT, then
6.28 seconds B=18.84 µT, then
6.28 seconds B=25/12 µT, then
6.28 seconds B=37.68 µT, then
6.28 seconds B=94/20 µT, then
720.17 seconds B=25.12 µT.

It applies that $T_1$=43.96 seconds and $T_2$=27.17 seconds. The ratio $T_1:T_2$=1.62 (rounded). Furthermore, the control apparatus is programmed in such a way that 49 repetitions are carried out. The application time thus takes a total of 58.09 minutes. A cycle of $T_1$ and $T_2$ lasts 71.13 seconds.

Alternatively, 31 repetitions of the cycle $T_1+T_2$ can also take place, which corresponds to a total application time of 36.75 minutes.

The magnetic field strengths lie between 3 and 100 µT (both in the time period $T_1$ and in the time period $T_2$), i.e. on the order of magnitude of the earth's magnetic field. After reaching the maximum field strength of 94.20 µT, the field strength is reduced to 25.12 µT at the end of the time period $T_1$. Overall, it has been found that with this signal course a particularly good increase in the well-being of the patient can be achieved.

Figure 2:
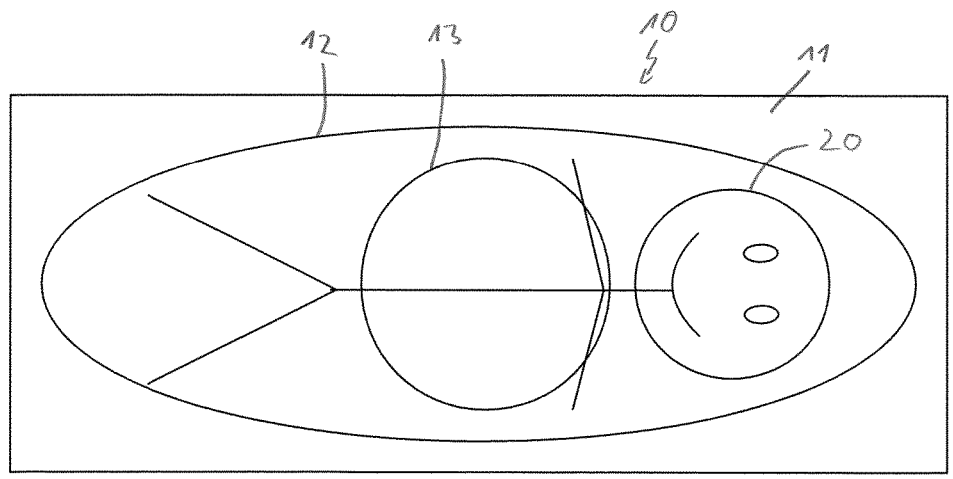
FIG. 2 shows an applicator according to an embodiment of the invention for applying the magnetic field.

FIG. 2 shows an applicator 10 according to an embodiment of the invention, on which a patient 20 is positioned. The applicator 10 comprises a mat 11 in which a first conductor coil 12 (with an oval or elliptical cross-section) and a second conductor coil 13 (with a round cross-section) are embedded. The mat 10 has a surface of (about) 220 cm*120 cm and is (approximately) 2 to 3 cm thick and comprises a foam body. The conductor coils 12, 13 can be incorporated into this foam. The first coil 12 with the oval cross-section has a larger cross-sectional area. The cross-sectional area is designed in such a way that the entire body area of the patient can be covered so that the magnetic field can be applied in the region of the entire body of the patient.

For example, a longer diameter of the coil 12 is 190 to 220 cm long. A shorter diameter is, for example, 80 to 110 cm long.

The smaller coil 13 with the round cross-section is arranged such that it covers approximately the abdominal or torso area of the patient (in particular the solar plexus). For this purpose, the diameter of the small coil 13 is smaller (for example by at least 5% or at least 10%) than the shorter diameter of the first coil 12. The center of symmetry of both coil cross sections is (approximately) in the solar plexus region. The entire body of the patient can be covered on the one hand with the coils 12, 13. On the other hand, a superposed magnetic field can be generated in the solar plexus region or torso region.

Figure 3:
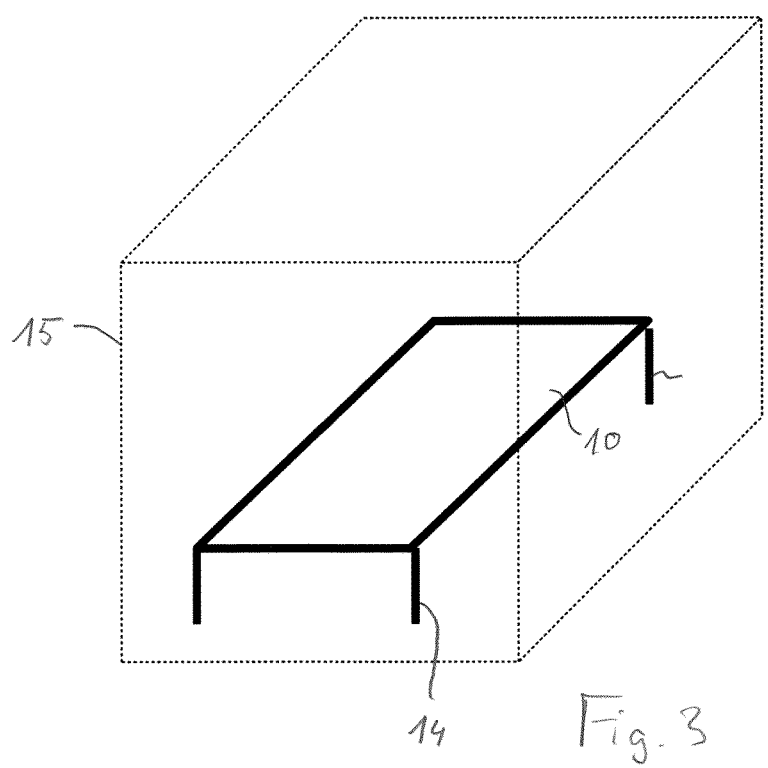
FIG. 3 shows a magnetic field therapy apparatus according to an embodiment of the invention.

In FIG. 3, the applicator 10 is placed on a patient couch 14. The patient couch 14 is surrounded by a shielding 15 so that external electromagnetic fields, for example electrosmog, can be shielded from treated patients. The shielding 15 can be used to prevent the therapy of the patient from being influenced or disturbed by external electromagnetic fields.

It can thus be achieved that the entire body of a patient is located in the region of influence of the generated magnetic field, without external electromagnetic interference fields. The apparatus thus permits a whole-body treatment, wherein the therapeutic effect is achieved by the appropriate modulation of the current intensity in the conductor coils and thus the magnetic field strength and also the induced electric fields. In this case, the current intensity for the conductor coils is adjusted by the control apparatus in such a way that the desired magnetic field strengths can be generated.

For example, corresponding programs can be stored (saved) in the control apparatus, so that the course of the magnetic field strength, as shown for example in FIG. 1, can be realised. It is possible to store (or save) two or more such programs in the same apparatus.

In order to control the magnetic field strength, the control apparatus comprises corresponding (generally known) structures, for example a control unit (e.g. microprocessor) and/or a display and/or an input means (e.g. touchscreen) and/or signal devices such as LEDs or acoustic signal devices and/or a memory device (memory chip).

The shielding 15 is preferably designed as an enclosure, i.e. it consists of a plurality of walls which surround the couch 14. The shielding 15, in particular its walls, can be constructed from perforated plates (not shown in the drawings).

The provided magnetic fields are preferably homogeneous. In so far as field strength values are stated, these preferably relate to a value which is measured in the center of the respective coil or a support surface for the patient.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed.

LIST OF REFERENCE NUMERALS

10 Applicator
11 Mat
12 First coil
13 Second coil
14 Patient couch
15 Shielding
20 Patient

The invention claimed is:

1. A magnetic field therapy apparatus, comprising:
a magnetic field generating apparatus for generating a magnetic field which can be applied to a patient, the magnetic field having a magnetic field strength; and
a control apparatus for controlling the magnetic field strength such that a stepwise increase of the magnetic field strength takes place during a first time period ($T_1$), the first time period ($T_1$) comprising at least three increment steps including a minimum step and a maximum step, and a constant magnetic field strength is set during a second time period ($T_2$), the second time period succeeding the maximum step of the first time period, and the constant magnetic field strength being greater than a magnetic field strength of the minimum step;
wherein a ratio of the first time period ($T_1$) to the second time period ($T_2$) corresponds to a rounded value of the golden section +/−0.1, the rounded value being 1.6180339887.

2. A magnetic field therapy apparatus according to claim 1, further comprising at least one battery for providing a direct current for generating the magnetic field.

3. A magnetic field therapy apparatus according to claim 1, wherein the control apparatus is designed for readjusting the magnetic field strength.

4. A magnetic field therapy apparatus according to claim 1, further comprising a shielding device for shielding electromagnetic fields, wherein the shielding device comprises at least one perforated plate and/or a fabric web and/or is at least partially designed as a tent or housing.

5. A magnetic field therapy apparatus according to claim 1, wherein:
in the first time period ($T_1$), a time course of a magnetic signal comprises an increase in the magnetic field strength by specific field strength increments ($\Delta B_1$, $\Delta B_2$, . . . $\Delta B_n$.) after specific time intervals ($\Delta t_1$, $\Delta t_2$, . . . $\Delta t_n$,), and/or
the increase in the magnetic field strength respectively takes place after identical time intervals, and/or
generatable magnetic field strengths are between 0 µT and 150 µT and/or incremental increments for the magnetic field strength lie between 2 µT and 60 µT and/or time intervals between the increment steps lie between 5 and 8 seconds.

6. A magnetic field therapy apparatus according to claim 1, wherein the field strength in the second time period ($T_2$) is 15 to 40 µT.

7. A magnetic field therapy apparatus according to claim 1, wherein:
the first time period ($T_1$) is 28 to 58 seconds, and/or
a cycle of the first ($T_1$) and the second ($T_2$) time period is repeated 40 to 58 times or 30 to 42 times, and/or
a total duration of an application lasts 50 to 66 minutes or 30 to 42 minutes.

8. A magnetic field therapy apparatus according to claim 1, wherein the magnetic field strength in the second time period ($T_2$) is 5 to 13 times as large as the magnetic field strength of the minimum step in the first time period ($T_1$), and/or 0.15 to 0.40 times as large as a magnetic field strength of the maximum step in the first time period ($T_1$).

9. A magnetic field therapy apparatus according to claim 1, wherein:
the magnetic field generating apparatus comprises a first conductor coil and a second conductor coil, wherein the first conductor coil is oval or elliptical and/or has a maximum diameter of 1.5 to 2.0 meters, and/or
the second conductor coil has a round cross-section and/or a cross-section which is smaller than a cross-section of the first coil, and/or
the second conductor coil is concentric with the first conductor coil.

10. A magnetic field therapy apparatus according to claim 1, wherein the magnetic field generating apparatus comprises a mat in which at least one conductor coil is embedded.

11. A magnetic field therapy apparatus according to claim 1, wherein the ratio of the first time period ($T_1$) to the second time period ($T_2$) corresponds to the rounded value of the golden section +/−0.01.

12. A magnetic field therapy apparatus according to claim 6, wherein the magnetic field strength in the second time period ($T_2$) is 20 to 30 µT.

13. A magnetic field therapy apparatus according to claim 12, wherein the magnetic field strength in the second time period ($T_2$) is 25.12 µT.

14. A method for generating a magnetic field, using the magnetic field therapy apparatus according to claim 1, wherein the magnetic field strength is increased stepwise in the first time period ($T_1$) and the magnetic field strength generated in the second time period ($T_2$) is constant, wherein the ratio of the first ($T_1$) to the second ($T_2$) time period corresponds to the rounded value of the golden section +/−0.1.

15. A method according to claim 14, wherein:
in the first time period ($T_1$), a time course of the magnetic field strength comprises an increase in the magnetic field strength by specific field strength increments ($\Delta B_1$, $\Delta B_2$, . . . $\Delta B_n$.) after specific time intervals ($\Delta t_1$, $\Delta t_2$, . . . $\Delta t_n$,), and/or
in the first time period ($T_1$) the increase in the magnetic field strength is effected for each increment step after identical time intervals, and/or
in the first time period ($T_1$) generated magnetic field strengths are between 0 µT and 150 µT and/or incremental increments for the magnetic field strength are set between 2 µT and 60 µT and/or time intervals between the increment steps are set between 5 and 8 seconds.

16. A method according to claim 14, wherein the magnetic field strength is readjusted.

17. A method according to claim 14, wherein:
the magnetic field strength in the second time period ($T_2$) is 15 to 40 µT, and/or
the first time period ($T_1$) is 28 to 58 seconds, and/or
a cycle of the first and second time period is repeated 40 to 58 times or 30 to 42 times, and/or
a total duration of an application is 50 to 66 minutes or 30 to 42 minutes, and/or
the magnetic field strength in the second time period ($T_2$) is 5 to 13 times as large as the magnetic field strength at the minimum step in the first time period ($T_1$), and/or 0.15 to 0.40 times as large as the magnetic field strength at the maximum step in the first time period ($T_1$).

18. A method according to claim 14, wherein a direct current for generating the magnetic field is fed from a battery.

19. A method according to claim 14, wherein the ratio of the first time period ($T_1$) to the second time period ($T_2$) corresponds to the rounded value of the golden section +/−0.01.

20. A method according to claim 14, wherein the magnetic field strength in the second period ($T_2$) is 20 to 30 µT.

* * * * *